United States Patent [19]
Mihashi

[11] Patent Number: 5,847,806
[45] Date of Patent: Dec. 8, 1998

[54] OPHTHALMOLOGICAL APPARATUS FOR FORMING A SECTIONAL IMAGE SIGNAL OF MEASUREMENT OBJECT

[75] Inventor: Toshifumi Mihashi, Tokyo, Japan

[73] Assignee: Kabushiki Kaisha Topcon, Tokyo, Japan

[21] Appl. No.: 893,376

[22] Filed: Jul. 21, 1997

[30] Foreign Application Priority Data

Jul. 21, 1996 [JP] Japan ................................. 8-209132

[51] Int. Cl.$^6$ ..................................................... A61B 3/10
[52] U.S. Cl. ................................. 351/221; 351/206
[58] Field of Search ............................. 351/205, 206, 351/210, 211, 212, 221; 356/35.5, 345, 348, 349, 357, 358, 359

[56] References Cited

U.S. PATENT DOCUMENTS 4,886,351  12/1989  Sabban et al. .......................... 351/221

Primary Examiner—Huy Mai
Attorney, Agent, or Firm—Baker & Botts, L.L.P.

[57] ABSTRACT

The present invention relates to ophthalmological apparatuses more specifically intends to provide an ophthalmological apparatus for forming a sectional image signal of a measurement object part within the subject's eye. A luminous flux separating means separates light from a first fiber into a reference optical fiber and a measuring optical fiber and a reference reflecting mirror reflects light from the reference optical fiber, and a detecting optical fiber combines light emitted from the measuring optical fiber and reflected from an eyeground of the subject's eye and led to the measuring optical fiber and light reflected by the reference reflecting mirror and led to the reference optical fiber and leads the combined light to a light receiver, and a light reflecting member detachably arranged in the optical path leads light from the light outgoing end surface of the measuring optical fiber arranged in the conjugate position to the eyeground of the subject's eye onto one optical path of the eyeground illumination system or the eyeground observation/photographing optical system.

11 Claims, 9 Drawing Sheets

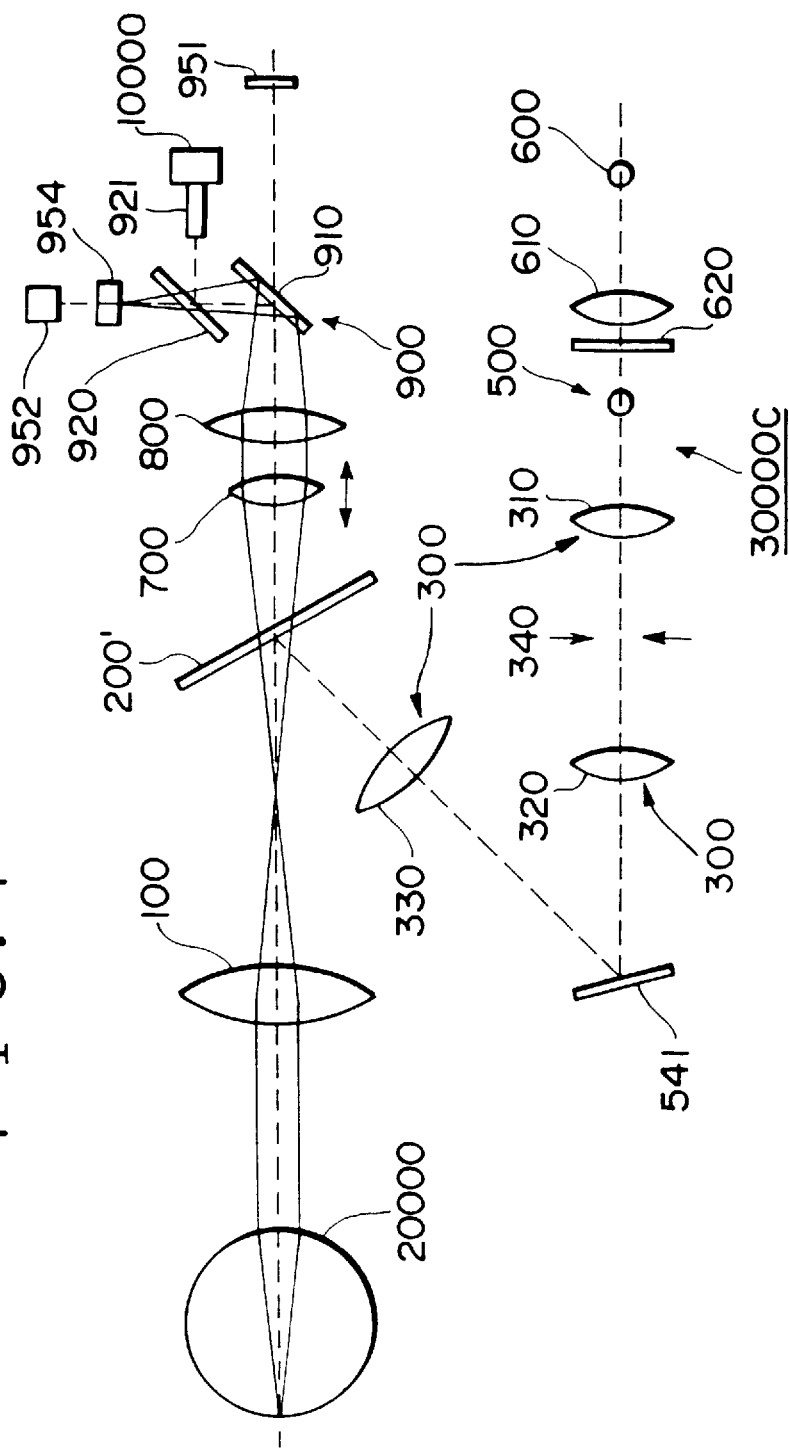

DEFECT OF NERVE LAYER

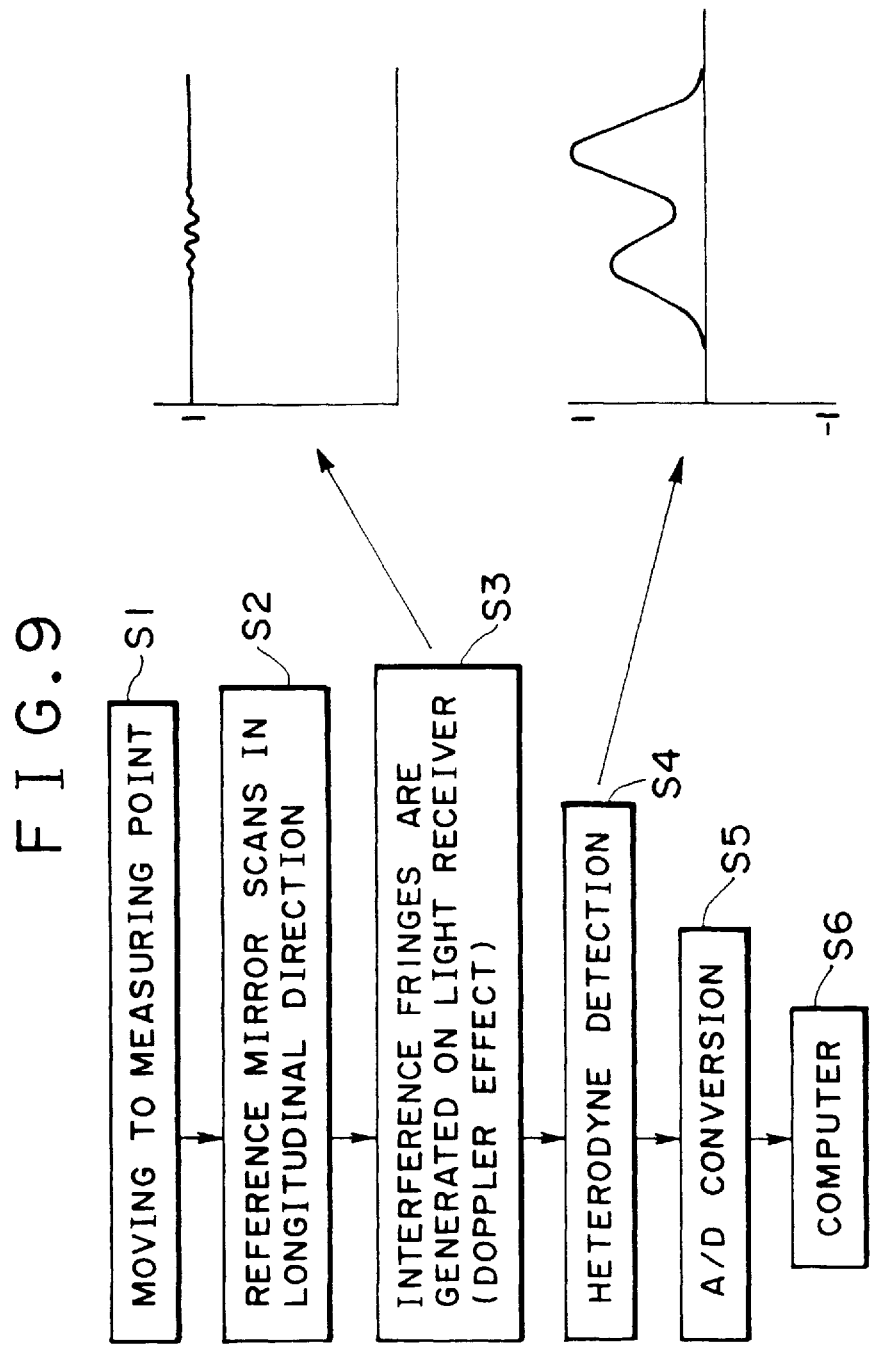

OPHTHALMOLOGICAL APPARATUS FOR FORMING A SECTIONAL IMAGE SIGNAL OF MEASUREMENT OBJECT

BACKGROUND OF THE INVENTION

The present invention relates to ophthalmological apparatuses, and more specifically, to an ophthalmological apparatus for forming a sectional image signal of an object of measurement within the subject's eye.

In the prior art, technology of obtaining a sectional image of an object of measurement within eyes of a living body is in that light of a light source with a coherence length being short is adopted, and the light source is separated into measuring luminous flux and reference luminous flux, and the measuring luminous flux is irradiated as a spot light to an object of measurement, and on the other hand, an optical path length of the reference luminous flux is varied.

The reference luminous flux and the measuring luminous flux being reflected and returned are combined and an interference signal is formed, and a sectional image of the object of measurement is obtained from the interference signal when a reflecting mirror installed at the reference optical path is moved.

Further the present applicant has filed a patent application regarding an apparatus where such an interference apparatus is assembled to a retinal camera (refer to JP-A 8-38422).

In the apparatus in the prior art as above described, however, t here is a problem that the optical arrangement is restricted moreover the apparatus can not be assembled simply to a regular retinal camera.

Further, there is another problem that the miniaturization is difficult moreover various bad influence is produced.

SUMMARY OF THE INVENTION

In the present invention, luminous flux separating means separates light from a first optical fiber into a reference optical fiber and a measuring optical fiber, and a reference reflecting mirror reflects the light from the reference optical fiber, and a detecting optical fiber combines light emitting from the measuring optical fiber and reflected by an eyeground of the subject's eye and led to the measuring optical fiber and light reflected from the reference reflecting mirror and led to the reference optical fiber and leads the combined light to a light receiver, and a light reflecting member detachably arranged on the optical path leads light from a light outgoing end surface of the measuring optical fiber arranged at a position conjugate with the eyeground of eyes to be examined onto one optical path of an eyeground illumination system or an eyeground observation/photographing optical system.

BRIEF DESCRIPTION OF THE DRAWINGS

FIG. 4 is a diagram showing configuration of a third embodiment according to the present invention;

FIG. 9 is a diagram showing function of the principle according to the present invention.

DESCRIPTION OF THE PREFERRED EMBODIMENTS

Principle

Here the principle of the interference technology applied to the present invention will be described.

Figure 7:
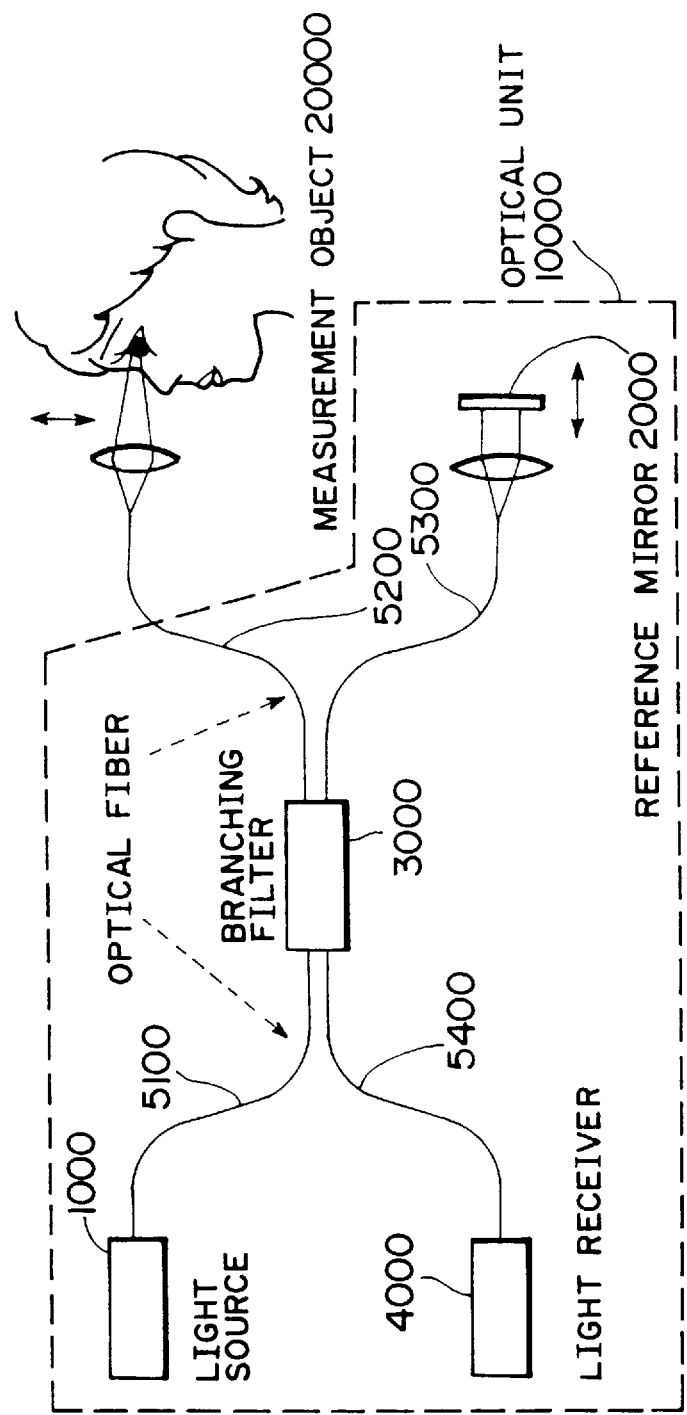
FIG. 7 is a diagram showing configuration of principle of an optical unit for measuring light interference according to the present invention.

As shown in FIG. 7, an optical unit 10000 for measuring light interference comprises a light source 1000, a reference mirror 2000, a branching filter 3000, a light receiver 4000 and an optical fiber 5000.

The optical fiber 5000 comprises a first optical fiber 5100 for leading light from the light source 1000, a measuring optical fiber 5200 for leading light to a measurement object 20000, a reference optical fiber 5300 for leading light to the reference mirror 2000, and a detecting optical fiber 5400 for leading light to the light receiver 4000.

As the light source 1000, a light source having coherence length as short as about 20 nm or less, e.g., 840 nm is utilized. In the light source 1000, a super luminescence diode (SLD) may be used.

The branching filter 3000 separates light from the first optical fiber 5100 into the reference optical fiber 5300 and the measuring optical fiber 5200. In addition, the branching filter 3000 corresponds to the luminous flux separating means.

The branching filter 3000 has also function of combining light reflected from the measurement object 20000 and led by the measuring optical fiber 5200 and light reflected from the reference mirror 2000 and led by the reference optical fiber 5300 and leading the combined light to the detecting optical fiber 5400.

The reference mirror 2000 is moved and controlled so that the optical path length from the branching filter 3000 to the reference mirror 2000 becomes basically equal to the optical path length from the branching filter 3000 to the eyeground of the eye being the measurement object 20000. In addition, the reference mirror 2000 corresponds to the reference reflecting mirror.

The eyeground of the eye being the measurement object 20000 and the outgoing end surface of the measuring optical fiber 5200 are in conjugate positions in geometrical optics.

The measurement reflection luminous flux by the measuring optical fiber 5200 and the reference reflection luminous flux by the reference optical fiber 5300 are combined and subjected to interference and the combined light is led to the light receiver 4000.

As the light receiver 4000, single photoelectric element capable of being measured in point is adopted.

Among the reference reflection luminous flux and the measurement reflection luminous flux, plural pieces of luminous flux being equal in the optical path length are in interference with each other and incident on the light receiver 4000. In other words, only component of reflected light from the structure of the eyeground being in the optical path length equal to that of the reference optical path including the side of the reference mirror 2000 contributes to the interference.

Consequently as the reference mirror 2000 is moved in the direction of the optical axis of the reference optical path, the reflection part contributing to the interference in the eyeground varies. Range in the depth direction of the eyeground contributing to the interference is determined depending on the coherence length of the used light source.

On account of the Doppler effect due to the scanning of the reference mirror 2000, the wavelength of the reference light varies slightly. Consequently the interference signal from the light receiver 4000 becomes a beat signal, and the sectional image signal can be extracted by the heterodyne light detection of the interference signal.

Figure 8:
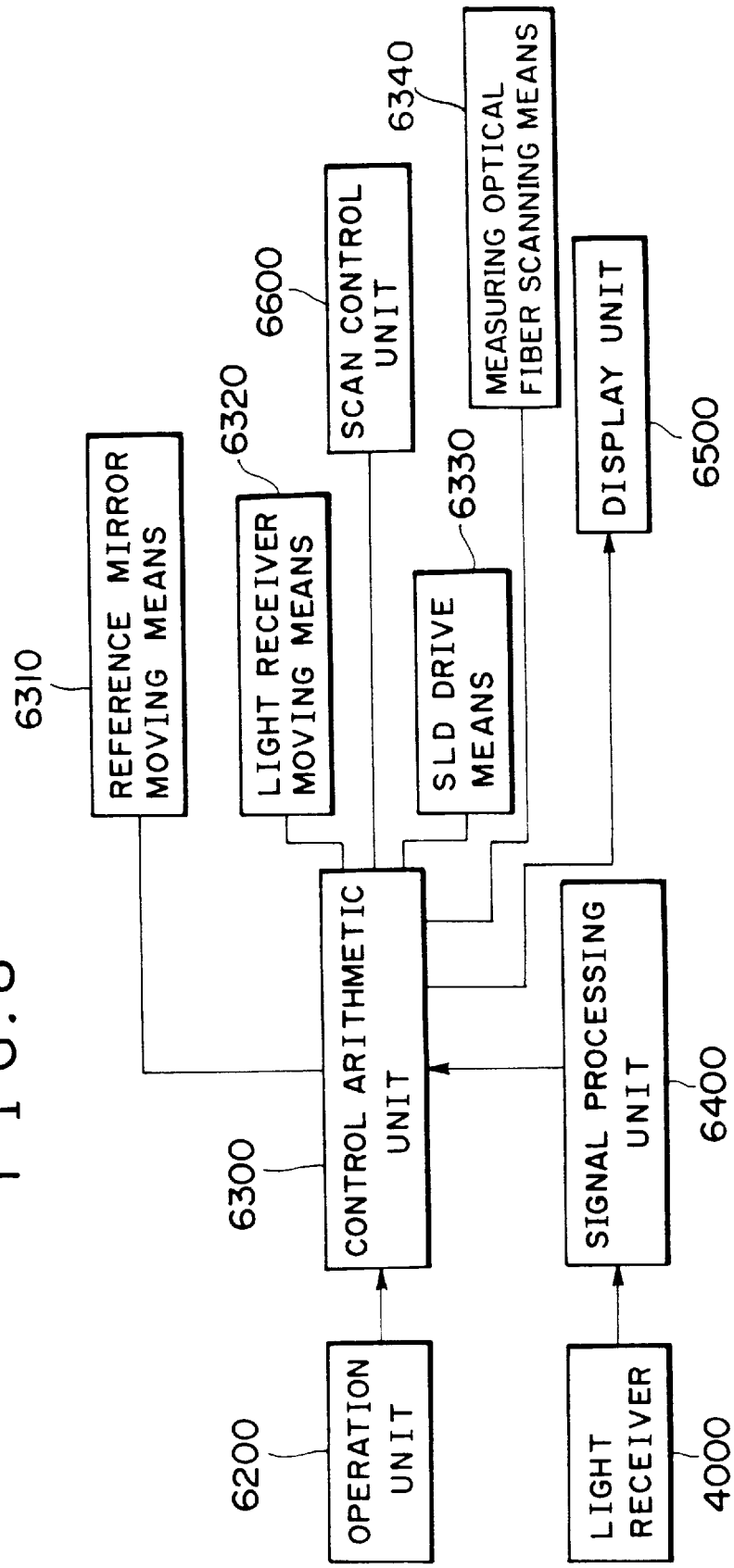
FIG. 8 is a block diagram showing the electrical configuration of the principle according to the present invention.

Next the electric configuration of the principle will be described based on FIG. 8.

The electric configuration of the principle is constituted by the light receiver 4000, an operation unit 6200, a control arithmetic unit 6300, a signal processing unit 6400, a display unit 6500 and a scan control unit 6600.

The operation unit 6200 is that where a user inputs a desired operation command.

The control arithmetic unit 6300 conducts operation for image formation and the whole control processing, particularly performs control of the light source 1000 and the reference mirror 2000 and scan of the measuring optical fiber 5200. A reference mirror moving means 6310, a light receiver moving means 6320, SLD driving means 6330 and a measuring optical fiber scanning means 6340 are connected to the control arithmetic unit 6300.

The reference mirror moving means 6310 moves the reference mirror 2000 in the optical axis direction by prescribed amount based on a drive signal of the control arithmetic unit 6300. The light receiver moving means 6320 moves the light receiver 4000 in the direction orthogonal to the element direction of the light receiver 4000 by prescribed amount based on a drive signal of the control arithmetic unit 6300. In the reference mirror moving means 6310 and the light receiver moving means 6320, a suitable linear moving mechanism is adopted.

The SLD driving means 6330 drives the light source 1000 constituted by SLD and generates light with a short coherence distance.

The display unit 6500 is constituted by display devices, and outputs a sectional image signal of an eyeground by a signal from the control arithmetic unit 6300.

Here, observation of a concrete eyeground will be described based on FIG. 9.

First, in step 1 (hereinafter referred to as "S1"), a measurement point is moved to an eyeground of an eye being a measurement object 20000. Next in S2, a reference mirror 2000 is scanned in the longitudinal direction. If the scan is executed in S2, interference fringes are generated on a light receiver 4000 in S3.

Doppler effect is produced by scan of the reference mirror 2000 in S2, and in S4, a signal processing unit 6400 performs heterodyne detection of a signal from the light receiver 4000 and in S5, the signal processing unit 6400 performs A/D conversion of a signal obtained in S4 and outputs the converted signal to a control arithmetic unit 6300.

The signal processing is in that a scan control unit 6600 performs the lateral scan on a measurement object 20000 at each measuring point based on a signal from the control arithmetic unit 6300 as hereinafter described, and the control arithmetic unit 6300 performs operation based on these signals inputted in each step and outputs a sectional image signal of the measurement object, and the sectional image of the measurement object 20000 is displayed by a display unit 6500.

Embodiments

Embodiments of an ophthalmological apparatus of the present invention applied to a retinal camera will be described based on the accompanying drawings.

A retinal camera is used for inspection of an eyeground, which is an essential inspection for a disease of an eyeground such as a retina, a choroid coat, an optic nerve or the like. The retinal camera is an apparatus capable of observing two-dimensional image of the eyeground in a photograph or in real time by a monitor.

Next, relation of an optical unit 10000 for measuring light interference and an optical system of a retinal camera 30000 will be described in detail.

Optical System 30000A of a Retinal Camera in First Embodiment

Figure 1:
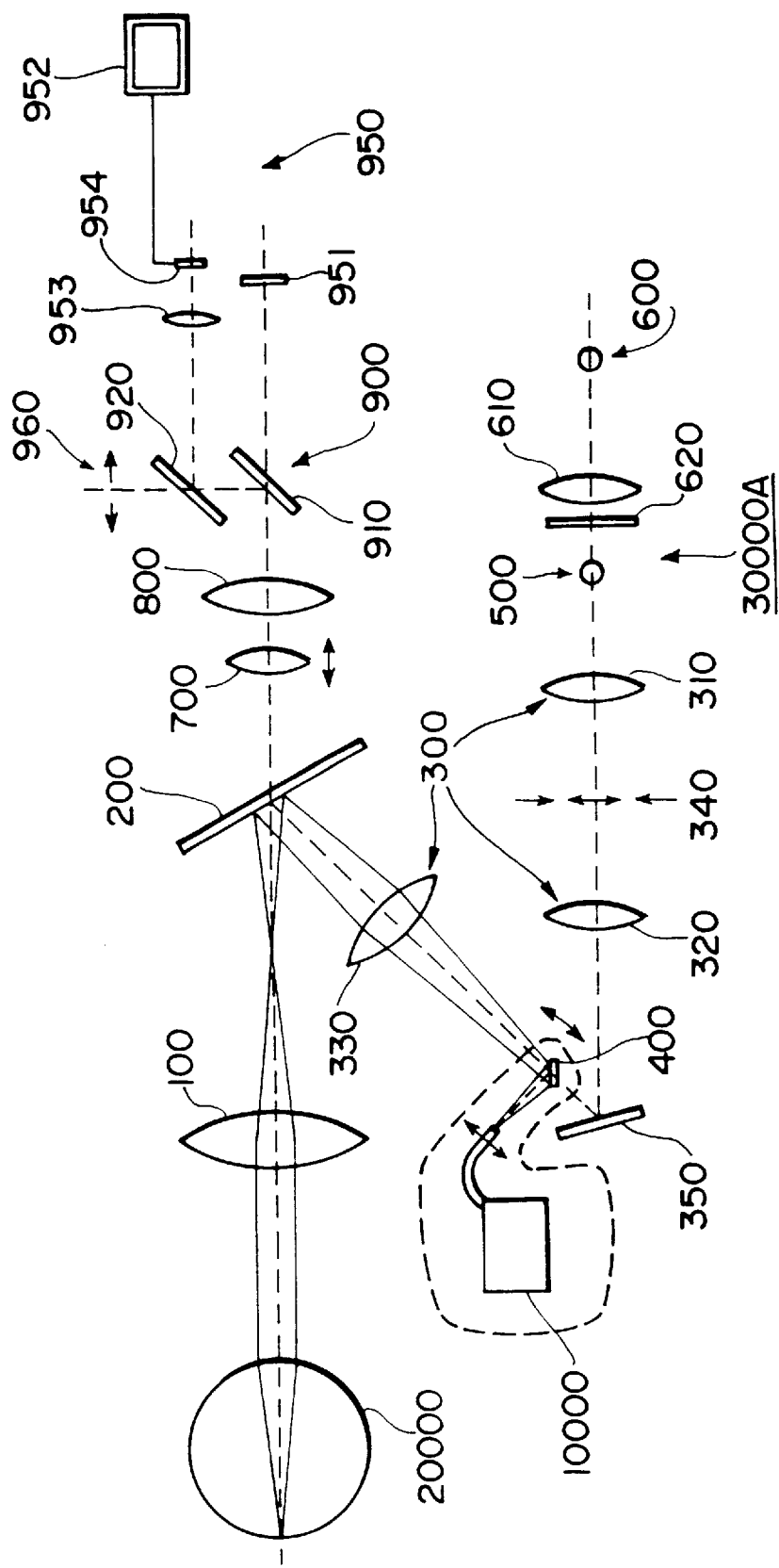
FIG. 1 is a diagram showing configuration of a first embodiment according to the present invention.

The basic configuration of an optical system 30000A of a retinal camera in a first embodiment will be described based on FIG. 1. The optical system 30000A of the retinal camera in the first embodiment comprises an objective lens 100, a wavelength selective element 200, a relay lens arrangement 300, a turning-up mirror 400, a photographing light source 500, an observation light source 600, a focusing lens 700, an image forming lens 800, a dichroic mirror 900 and an image pickup means 950.

Figure 2:
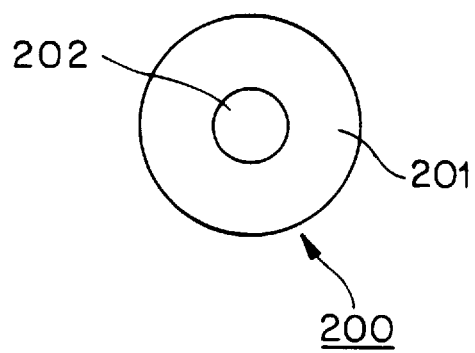
FIG. 2 is a diagram showing a wavelength selective element 200 in the first embodiment.

As shown in FIG. 2, an outer circumferential part 201 of the wavelength selective element 200 is an ordinary reflecting mirror for reflecting both visible light and infrared light, and a dichroic mirror at a central part 202 reflects infrared light of wavelength in the vicinity of 840 nm and transmits near infrared light of wavelength in the vicinity of 800 nm and visible light. In the case of the eyeground observation by near infrared light and the eyeground photographing by visible light, the dichroic mirror functions as a perforated mirror, and for the infrared light of 840 nm being light for measuring interference, it functions as an ordinary mirror.

Referring again to FIG. 1, the relay lens arrangement 300 comprises a first relay lens 310, a second relay lens 320 and a third relay lens 330.

The first relay lens 310 and the second relay lens 320 are inserted between the photographing light source 500 and the optical unit 10000 for measuring light interference so that light from the photographing light source 500 and the observation light source 600 is led to the optical unit 10000 for measuring light interference. In addition, a ring diaphragm 340 is inserted between the first relay lens 310 and the second relay lens 320. Also light from the second relay lens 320 is reflected by a mirror 350 and led to the optical unit 10000 for measuring light interference. The third relay lens 330 is inserted between the optical unit 10000 for measuring light interference and the wavelength selective element 200.

The turning-up mirror 400 is formed in the optical path from the photographing light source 500 and the observation light source 600 to the wavelength selective element 200. When an eyeground is observed or photographed, the turning-up mirror 400 is turned up and removed, and when the interference is measured by the optical unit 10000 for measuring light interference, it is inserted and arranged within the optical path and can take light from the optical unit 10000 for measuring light interference.

In place of the tuning-up mirror 400, a wavelength selective mirror may be used. The wavelength selective mirror corresponds to a wavelength selective reflecting member. In this case, the wavelength selective mirror has characteristics that infrared light of wavelength in the vicinity of 840 nm is reflected and near infrared light of wavelength in the vicinity of 800 nm and visible light are transmitted.

Light from the photographing light source 500 is incident on the relay lens arrangement 300, but light from the observation light source 600 is incident on the relay lens arrangement 300 through a condenser lens 610 and an infrared filter 620. Consequently among light from the observation light source 600, luminous flux transmitting the infrared filter 620 is in the wavelength band of near infrared in the vicinity of 800 nm.

The focusing lens 700 is inserted between the wavelength selective element 200 and the image pickup means 950 so as to focus on the eyeground of the subject. In interlocking with the moving of the focusing lens 700, also the turning-up mirror 400 can be moved along the optical axis. According to the moving, if the focusing adjustment is performed on the eyeground image by the focusing lens 700, it follows that the end surface of the measuring optical fiber 5200 of the optical unit 10000 for measuring light interference is automatically arranged in the conjugate position to the eyeground of the subject.

The image forming lens 800 forms an image of the eyeground light transmitting the wavelength selective element 200 onto the image pickup means 950.

The image pickup means 950 comprises a photographic film 951 and an infrared monitor 952. The optical path from the eyeground of the eye being the measurement object 20000 to the image pickup means 950 corresponds to the eyeground observation/photographing optical system. Also the optical path from the observation light source 600 to the eyeground of the eye being the measuring object 20000 corresponds to the eyeground illumination system.

The dichroic mirror 900 comprises a first dichroic mirror 910 and a second dichroic mirror 920. The first dichroic mirror 910 transmits almost visible light used in the eyeground photographing and reflects a part of visible light and infrared light (including near infrared light), and an image of the visible light transmitting the first dichroic mirror 910 is formed on the photographic film 951. Further the infrared light reflected by the first dichroic mirror 910 is incident on the second dichroic mirror 920. The second dichroic mirror 920 reflects infrared light and transmits visible light, and an image of the reflected infrared light is formed through a photographing relay lens 953 on a CCD sensor 954 of infrared sensing.

An eyeground image signal obtained in the CCD sensor 954 can be monitored by a monitor device 952.

Luminous flux from a fixed indicator 960 to determine the viewing direction of the subject transmits the second dichroic mirror 920 and is reflected by the first dichroic mirror 910 and is projected to the subject.

In the optical system 30000A of the retinal camera in the first embodiment constituted as above described, the optical path from the photographing light source 500 and the observation light source 600 to the optical unit 10000 for measuring light interference can be divided in light wave by the turning-up mirror 400. Further the photographing optical path of the retinal camera and the optical path of the optical unit 10000 for transmitting light interference can be divided in light wave by the wavelength selective element 200.

The eyeground of the eye being the measurement object 20000 and the outgoing end surface of the measuring optical fiber 5200 of the optical unit 10000 for measuring light interference are arranged in conjugate positions.

The reference optical path formed by the reference mirror 2000 and the reference optical fiber 5300 is determined in consideration of the optical path length of the optical system 30000A of the retinal camera in the first embodiment.

Here, the measuring optical fiber 5200 of the optical unit 10000 for measuring light interference is moved and scanned in one dimension or in two dimensions by the scan control unit 6600 as above described. The measuring luminous flux is moved on the eyeground by the scan and the interference is measured in each measuring point and the sectional image of the eyeground in one dimension or in two dimensions can be obtained by the interference measurement. When the measuring optical fiber 5200 is scanned in such manner, in place of the moving scan of the projection measuring luminous flux to the eyeground, the fixed indicator 960 is moved and scanned by the scan control unit 6600, and the same function as that of the above-mentioned moving scan can be done by varying the viewing direction of the subject and by varying the eyeground position to which the measuring luminous flux attains.

The optical system 30000A of the retinal camera in the first embodiment as above described has predominant effect that the arrangement of the eyeground camera need not be changed.

Optical System 30000B of a Retinal Camera in Second Embodiment

Figure 3:
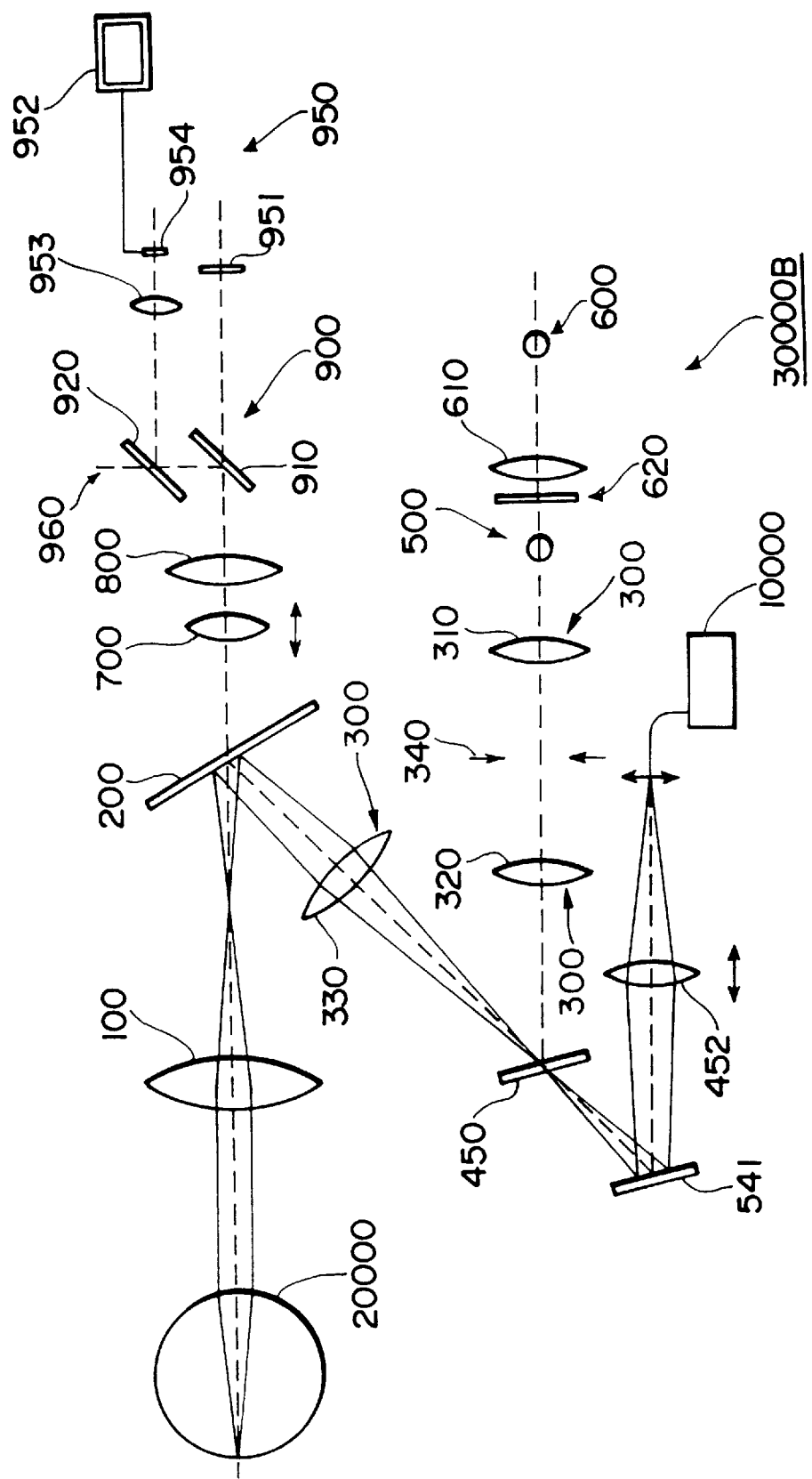
FIG. 3 is a diagram showing configuration of a second embodiment according to the present invention.

The basic configuration of an optical system 30000B of a retinal camera in a second embodiment will be described based on FIG. 3. The optical system 30000B of the eyeground camera in the second embodiment comprises an objective lens 100, a wavelength selective element 200, a relay lens arrangement 300, a dichroic mirror 450 for optical unit for measuring light interference, a photographing light source 500, an observation light source 600, a focusing lens 700, an image forming lens 800, a dichroic mirror 900 and an image pickup means 950.

The dichroic mirror 450 for optical unit for measuring light interference is adopted in place of the turning-up mirror 400 in the first embodiment. The dichroic mirror 450 for optical unit for measuring light interference transmits light of wavelength in the vicinity of 840 nm and reflects near infrared light of wavelength in the vicinity of 800 nm and visible light. Consequently infrared light from the photographing light source 500 and the observation light source 600 can be reflected and led to the wavelength selective element 200. Infrared light of wavelength in the vicinity of 840 nm transmits the dichroic mirror 450 for optical unit for measuring light interference and is reflected by a mirror 541 and then attains through a second focusing lens 452 to the outgoing end surface of a measuring optical fiber 520 of an optical unit 10000 for measuring light interference. The dichroic mirror 450 for optical unit for measuring light interference corresponds to the wavelength selective reflecting member.

The second focusing lens 452 can adjust the diopter in interlocking with the focusing lens 700.

When the outgoing end surface of the measuring optical fiber 5200 of the optical unit 10000 for measuring light interference is scanned, the eyeground image can be analyzed.

The optical system 30000B of the retinal camera in the second embodiment constituted as above described has effect that observation and photographing of the image of the eyeground and the interference measurement by the optical unit 10000 for measuring light interference can be performed simultaneously without necessitating a movable part such as a mirror.

Since other configuration, functions and the like of the second embodiment are similar to those in the first embodiment as above described, the detailed description shall be omitted.

Optical System 30000C of a Retinal Camera in Third Embodiment

The basic configuration of an optical system 30000C of a retinal camera in a third embodiment will be described based on FIG. 4. The optical system 30000C of the retinal camera in the third embodiment comprises an objective lens 100, a perforated mirror 200', a relay lens arrangement 300, a photographing light source 500, an observation light source 600, a focusing lens 700, an image forming lens 800, a dichroic mirror 900 and an image pickup means 950.

The dichroic mirror 900 comprises a first dichroic mirror 910 and a second dichroic mirror 920. The first dichroic mirror 910 reflects near infrared light of wavelength in the vicinity of 800 nm and infrared light of wavelength in the vicinity of 840 nm and transmits visible light. Also the second dichroic mirror 920 reflects infrared light of wavelength in the vicinity of 840 nm and transmits near infrared light of wavelength in the vicinity of 800 nm.

An image of the visible light transmitting the first dichroic mirror 910 is formed on a photographic film 951. Further light of wavelength in the vicinity of 800 nm reflected by the first dichroic mirror 910 is incident on the second dichroic mirror 920. The second dichroic mirror 920 reflects light of wavelength in the vicinity of 840 nm, and the reflected light passes through an optical fiber 921 and attains to a measuring optical fiber 5200 of the optical unit 10000 for measuring light interference.

An image of the near infrared light in the vicinity of 800 nm transmitting the second dichroic mirror 920 is formed on a CCD sensor 954 of infrared sensing.

An eyeground image signal obtained in the CCD sensor 954 can be monitored by a monitor device 952.

The dichroic mirror 900 corresponds to the wavelength selective reflecting member.

The optical system 30000C of the retinal camera in the third embodiment constituted as above described has effect that an optical system in a conventional retinal camera can be utilized in state kept intact.

In place of the second dichroic mirror 920, a turning-up mirror may be adopted. The turning-up mirror is constituted so that light from the observation light source 600 escapes and light from the photographing light source 500 is taken in.

Since other configuration, functions and the like of the third embodiment are similar to those in the first embodiment and the second embodiment as above described, the detailed description shall be omitted.

Figure 5A:
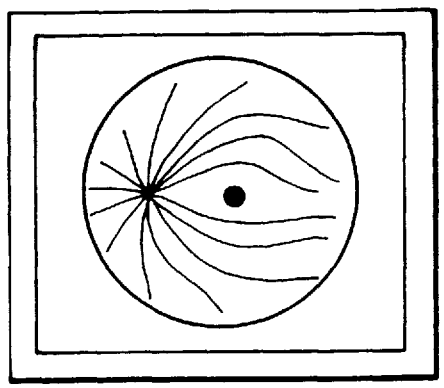
FIGS. 5(a) to 5(d) are diagrams explaining an eyeground image.
Figure 5B:
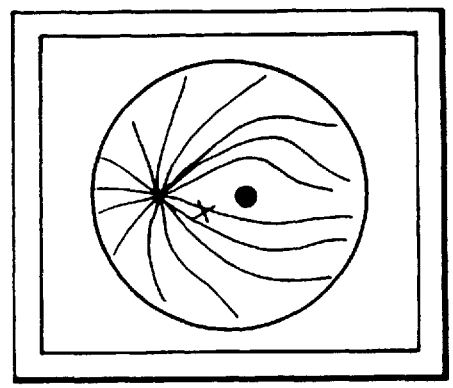
Figure 5C:
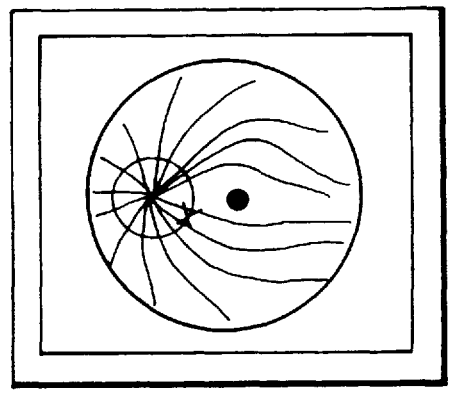
Figure 5D:
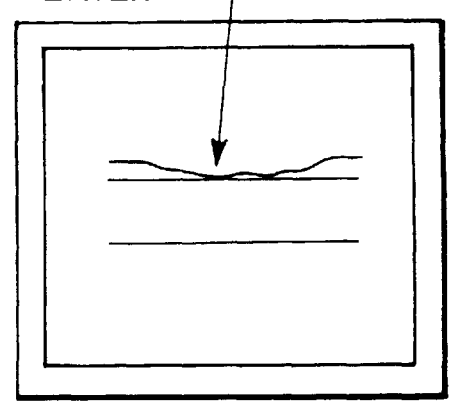
Figure 6:
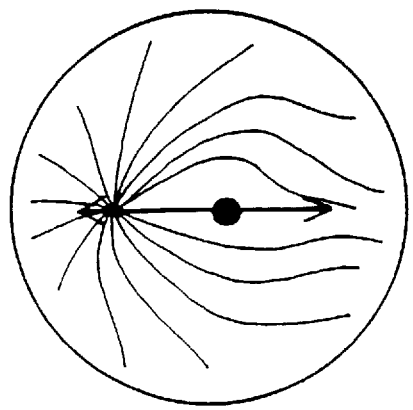
FIGS. 6(a) to 6(c) are diagrams explaining an eyeground image.
Figure 6:
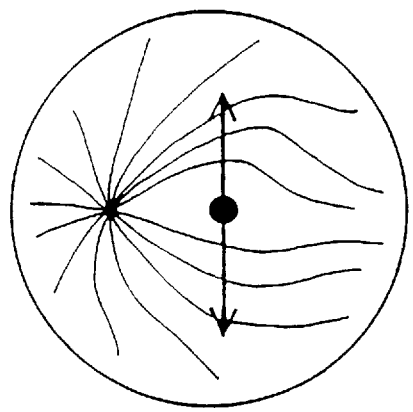
Figure 6:
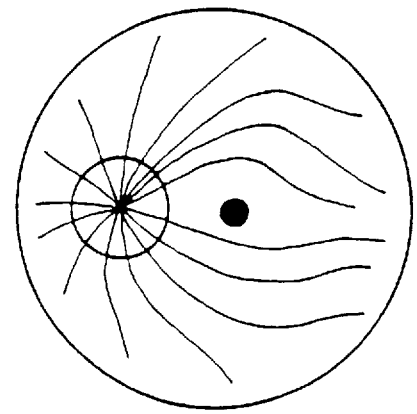

According to the retinal camera of this embodiment, as shown in FIG. 5 and FIG. 6, a macula, a papilla and a blood vessel can be observed clearly.

As shown in FIG. 5(a), first, cross lines (not shown) reflected on a monitor are used as a base level and the center point of measurement on the eyeground is determined, and if scan is performed based on the center point and measurement is started, a defect or the like in an optic nerve layer can be observed as shown in FIG. 5(d).

If the electric mark varying corresponding to the scan of the measuring optical fiber 5200 by the scan control unit 6600 as above described and indicating the scan position on the eyeground is displayed in overlapping with the eyeground image on the monitor, the measurement scan position on the eyeground can be observed.

If the above-mentioned electric mark is projected simultaneously with the photographing of the eyeground image, during the photographing of the eyeground image, the photographed image clearly indicating also the measurement position can be obtained.

Further the directions of scan may be the lateral direction as shown in FIG. 6(a), the longitudinal direction as shown in FIG. 6(b) and the circular direction as shown in FIG. 6(c).

In the above-mentioned embodiment, although the near infrared light in the vicinity of 800 nm for the eyeground observation and the infrared light in the vicinity of 840 nm used in the measurement are completely separated in wavelength by the dichroic mirror, if the dichroic mirror is partially made semitransparent characteristics regarding the near infrared light and the infrared light and further light for measuring the interference is partially incident on the CCD sensor 954 for the eye ground image observation, the light for measuring the interference can be observed in overlapping with the eyeground image and position of the luminous flux for measuring the interference scanned by the scan control unit 6600 can be observed and confirmed.

In the present invention constituted as above described, since the luminous flux separating means separates light from the first fiber into a reference optical fiber and a measuring optical fiber, and the reference reflecting mirror reflects light from the reference optical fiber, and the detecting optical fiber combines light emitted from the measuring optical fiber and reflected from the eyeground of the subject and led to the measuring optical fiber and light reflected by the reference reflecting mirror and led to the reference optical fiber and leads the combined light to the light receiver, and the light reflecting member detachably arranged in the optical fiber leads light from the light outgoing end surface of the measuring optical fiber arranged in conjugate position to the eyeground of the subject onto one optical path of the eyeground illumination system or the eyeground observation/photographing optical system, the present invention has the predominant effect that the apparatus can be simply installed to a retinal camera without limiting the optical arrangement.

What is claimed is:

1. An ophthalmological apparatus, comprising:
   (a) an eyeground illumination system for projecting eyeground illumination light along a first optical path to an eyeground of a subject's eye;
   (b) an eyeground observation/photographing optical system for observation and photographing along a second optical path of an eyeground illuminated by the eyeground illumination light;
   (c) an optical unit located in one of the first and second optical paths for measuring light interference, the optical unit comprising
      (1) a light source for emitting measurement light of short coherent length;
      (2) a first optical fiber for leading light from the light source;
      (3) a luminous flux separating means for separating and leading the light from the first optical fiber into a reference optical fiber and a measuring optical fiber, the measuring optical fiber having an outgoing end surface in conjugate position to the eyeground;
      (4) a reference reflecting mirror for reflecting the light from the reference optical fiber;
      (5) a detecting optical fiber for combining light emitted from the measuring optical fiber and reflected from the eyeground and led to the measuring optical fiber and light reflected by the reference reflecting mirror and led to the reference optical fiber; and
      (6) a light receiver for receiving the combined light from the detecting optical fiber;
   (d) a light reflecting member arranged in the one optical path for selectively directing light from the light outgoing end surface of the measuring optical fiber to the eyeground.

2. The apparatus according to claim 1, wherein the light reflecting member comprises a movable mirror.

3. The apparatus according to claim 2, wherein light interference is measured by the optical unit when the light reflecting member is properly positioned in the one optical path, and observation and photographing of the eyeground is performed when the light reflecting member is removed from the one optical path.

4. The apparatus according to claim 1, wherein the light reflecting member simultaneously directs (1) light from the light outgoing end surface of the measuring optical fiber, and (2) light from the eyeground illumination system to the eyeground.

5. The apparatus according to claim 4, wherein the light reflecting member comprises a wavelength selective reflecting member.

6. The apparatus according to claim 5, wherein the wavelength selective reflecting member comprises a wavelength selective mirror.

7. The apparatus according to claim 1, wherein the light reflecting member simultaneously directs (1) light from the light outgoing end surface of the measuring optical fiber, and (2) light from the eyeground to the eyeground observation/photographing optical system.

8. The apparatus according to claim 7, wherein the light reflecting member comprises a wavelength selective reflecting member.

9. The apparatus according to claim 8, wherein the wavelength selective reflecting member comprises at least one wavelength selective mirror.

10. The apparatus according to claim 8, wherein the wavelength selective reflecting member comprises a movable mirror.

11. In an ophthalmological apparatus for forming a sectional image signal of a measurement object, an optical unit for measuring light inference comprising:

(a) a light source for emitting measurement light of short coherent length;

(b) a first optical fiber for leading light from the light source;

(c) a luminous flux separating means for separating and leading the light from the first optical fiber into a reference optical fiber and a measuring optical fiber, the measuring optical fiber having an outgoing end surface in conjugate position to the eyeground of the subject's eye;

(d) a reference reflecting mirror for reflecting the light from the reference optical fiber;

(e) a detecting optical fiber for combining light emitted from the measuring optical fiber and reflected from the eyeground and led to the measuring optical fiber and light reflected by the reference reflecting mirror and led to the reference optical fiber; and (f) a light receiver for receiving the combined light from the detecting optical fiber.

* * * * *